United States Patent [19]

Miyazaki et al.

[11] Patent Number: 5,011,471
[45] Date of Patent: Apr. 30, 1991

[54] EXCRETIONS TREATING APPARATUS

[75] Inventors: Kazuoki Miyazaki, Odawara; Yasuo Noguchi; Naohiko Inoue, both of Yokohama; Morito Idemoto, Yokohama, all of Japan

[73] Assignee: Sumitomo Bakelite Company Limited, Tokyo, Japan

[21] Appl. No.: 399,549

[22] PCT Filed: Dec. 23, 1988

[86] PCT No.: PCT/JP88/01319

§ 371 Date: Aug. 16, 1989

§ 102(e) Date: Aug. 16, 1989

[87] PCT Pub. No.: WO89/05612

PCT Pub. Date: Jun. 29, 1989

[30] Foreign Application Priority Data

Dec. 24, 1987 [JP] Japan ................... 62-325506
May 17, 1988 [JP] Japan ................ 63-64020[U]

[51] Int. Cl.$^5$ .............................. A61B 17/20
[52] U.S. Cl. ........................ 604/22; 604/35; 606/127; 128/24 A
[58] Field of Search ............ 604/22, 27, 35, 48, 604/49, 319; 606/127, 128; 128/24 A

[56] References Cited

U.S. PATENT DOCUMENTS

| | | |
|---|---|---|
| 3,589,363 | 6/1971 | Banko . |
| 3,693,613 | 9/1972 | Kelman . |
| 3,805,787 | 4/1974 | Banko . |
| 4,045,859 | 9/1977 | Cooley et al. . |
| 4,063,557 | 12/1977 | Wuchinich et al. . |
| 4,417,578 | 11/1983 | Banko . |
| 4,516,398 | 5/1985 | Wuchinich . |
| 4,516,973 | 5/1985 | Telang . |
| 4,589,415 | 5/1986 | Haaga . |
| 4,682,979 | 7/1987 | Girouard . |
| 4,747,820 | 5/1988 | Hornlein et al. ............. 604/22 |
| 4,804,364 | 2/1989 | Dieras et al. ............. 604/22 |

FOREIGN PATENT DOCUMENTS

| | | |
|---|---|---|
| 237484 | 2/1962 | Australia . |
| 0001718 | 1/1979 | European Pat. Off. . |
| 0005719 | 12/1979 | European Pat. Off. . |
| 2733019 | 1/1979 | Fed. Rep. of Germany . |
| 61-293472 | 1/1986 | Japan . |

Primary Examiner—John D. Yasko
Attorney, Agent, or Firm—Browdy and Neimark

[57] ABSTRACT

An excretions treating apparatus comprises a horn (54) which is vibrated by ultrasonics, a pump (6) for pumping cleaning liquid into a passage defined between the horn (54) and a protection cover (13) covering the horn (54), and a suction passage (25) formed in the horn (54). The excrements in a rectum crushed and emulsified by the ultrasonic vibration of the horn (54) and the cleaning liquid is evacuated by a suction pump (12) through the suction passage.

18 Claims, 4 Drawing Sheets

EXCRETIONS TREATING APPARATUS

DESCRIPTION

1. Technical Field

The present invention relates to an excretions treating apparatus which can extract and remove excrements from a rectum of an inevacuative patient.

2. Background Art

A patient who needs a certain excretions treatment (to be called "a patient" hereinafter) has been treated with a laxative, a clyster, an anal stimulus and the like according to the condition of the patient. On the other hand, as to the inevacuative patient, a high pressure clyster, a removal of excrements, a suppository or the combination thereof has been applied. The condition of "inevacuative" means that it is impossible to evacuate without help of other person.

However, the above-described treatments arise the following problems.

In the high pressure clyster, a catheter and a large-sized-syringe are used to inject medical fluid into a patient's rectum through his anus so as to stimulate evacuation. However, in this case, there is a fear that a rectum wall is damaged In addition, if excrements is hard, the high pressure clyster cannot demonstrate its ability effectively, with the result that the evacuation cannot be fully conducted. Furthermore, it takes a too time to do this treatment, whereby the patient is considerably physical suffering.

In the removal of the excrements, fingers with a sanity glove worn are inserted directly through patient's rectum to scrape out the excrements. However, if excrements is hard, it is difficult to scrape them out completely, with the result that the evacuation cannot be fully conducted. In addition, there is a fear that a mucous membrane on the patient's rectum is damaged.

Suppository is almost useless for hard excrements.

In order to overcome the above-described problems, a suction type excretions treatment apparatus has been proposed, which is one of high pressure clyster methods (JP-A-61-293472). In this suction type excretions treatment apparatus, there are provided an outer pipe and a guide pipe which is slidable within the outer pipe. After the outer pipe has been inserted into the patient's rectum, the guide pipe is extended into the patient's rectum beyond an end portion of the outer pipe, and then the medical fluid is injected there through into the patient's rectum. After the excrements has been softened, the guide pipe is retracted to open the end portion of the outer pipe Then, the thus-softened excrements are extracted from the opened portion of the outer pipe by a vacuum pump into an external reservoir tank through the outer pipe.

However, since the excrement is softened simply by the medical fluid, this apparatus could not demonstrate its ability effectively for hard excrements.

DISCLOSURE OF INVENTION

Accordingly an object of the present invention is to provide an excretions treating apparatus which can solve these problems and is capable of a effective and safe full evacuation.

To this end, according to the present invention, an excretion treating apparatus comprises crushing means for crushing excrements by mechanical vibrations caused by ultrasonics, and extracting and excreting means for excreting the crushed excrements outside the patient's body.

According to another aspect of the present invention, an excretion treating apparatus comprises, in addition to the crushing means and the extracting and excreting means, medical fluid injection means for injecting medical fluid into excrements in the rectum to soften it.

According to the crushing means, even if the excrements is hard, it can be crushed and extracted readily and fully.

Then, a preferred embodiment of the present invention will be described hereinunder with reference to the accompanying drawings:

BEST MODE FOR CARRYING OUT THE INVENTION

Figure 1:
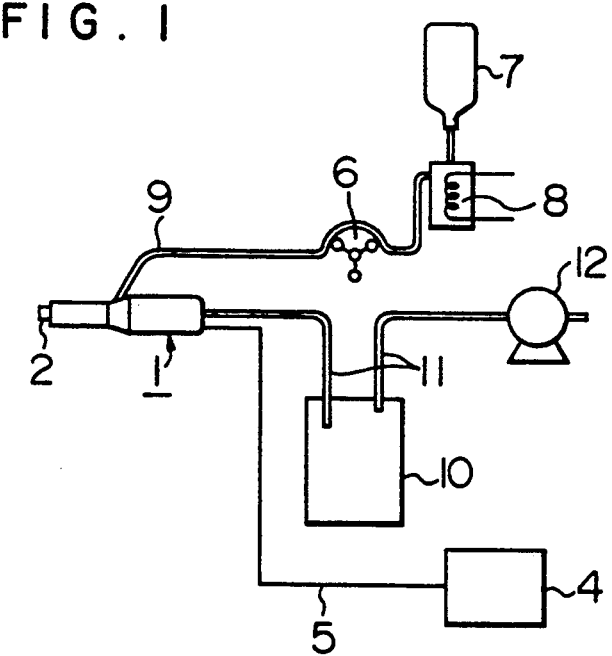
FIG. 1 is a view illustrating a pipe arrangement of an embodiment of the present invention.
Figure 2:
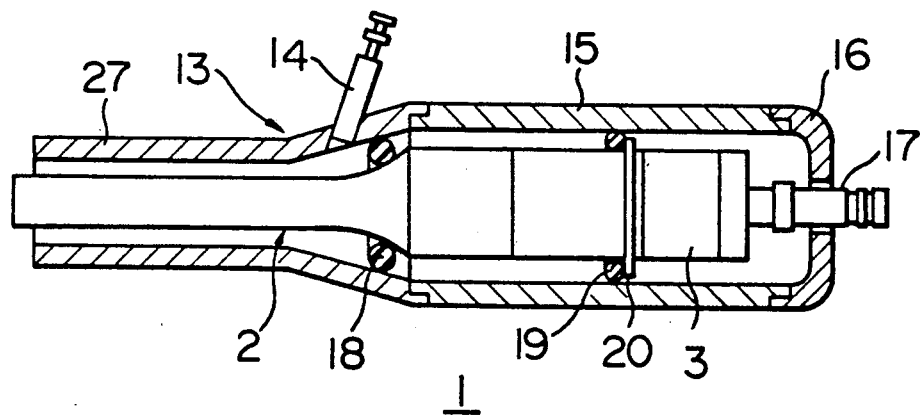
FIG. 2 is an enlarged cross-sectional view showing an insert shown in FIG. 1.
Figure 3:
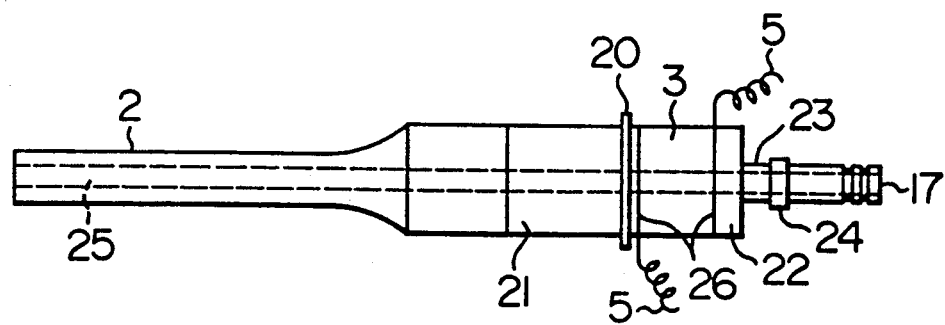
FIG. 3 is a front elevational view showing a horn shown in FIG. 2.

Referring to FIGS. 1 to 3, an excretion treating apparatus according to an embodiment of the present invention comprises an insert portion, an ultrasonic generating portion, an irrigation portion, and an extracting and excreting portion.

As shown in detail in FIG. 2, an insert 1 comprises a main body 15 and a horn 2 disposed within the main body 15. An elongate cylindrical extension portion of the horn 2 is surrounded by a protection cover 13 which is fitted to the main body 15. An irrigation nipple 14 for injecting cleaning liquid is screw mounted or fixed to the protection cover 13 by a screw or is inserted into the same. An irrigation tube 9 shown in FIG. 1 is connected to the irrigation nipple 14. An opening through which a suction nipple 17 passes is formed in a lid 16 disposed at the rear end portion of the main body 15. As shown in FIG. 1, a suction tube 11 is connected to the suction nipple 17.

A transducer 3 of an electrostrictive type or a magnetostrictive one is so disposed as to be positioned in contact with the horn 2. High-frequency electric power of ultrasonic area is supplied through a cable 5 and then the horn 2 is mechanically vibrated in ultrasonic manner. Reference numeral 4 represents an ultrasonic oscillator for generating high-frequency electric power. The cable 5 is electrically connected to the transducer 3 through an opening formed in the lid 16.

The protection cover 13 serves to prevent the horn 2 which is vibrated by the ultrasonic energy from contacting the anus or the wall of the rectum, and may be made of any material. It is preferable that the protection cover 13 is made of plastics, synthetic rubber, or combination thereof on purpose that it is smoothly inserted into the anus and that the patient does not feel cold. A lubricant such as jelly is applied to the outer surface of the protection cover 13 when used, if necessary. It is necessary for the protection cover 13 that a length of a straight portion 27 thereof corresponds to the length from the anus to the excrement in the rectum. In general it is 5 to 12 cm, preferably 10 cm. There is provided O-ring 18 (one or two) between a tapered horn portion in a down stream of the irrigation nipple 14 and an inner surface of the protection cover 13. The O-ring 18 prevents the cleaning liquid from flowing from a tubular cleaning liquid passage towards the transducer 3, which is defined between the horn 2 and the protection cover 13. The protection cover 13 may be connected to the main body 15 by an adhesive bonding, a screw mounting, or a fitting connection. In terms of convenience in replacement of the horn 2, it is preferable that they are connected to each other by the screw mounting or the fitting connection.

It is preferable that the main body 15 is made of a material which is non-corrosive against chemicals and light weight, and has high mechanical strength. Such material includes aluminum alloy, polysulfone resin, polyether sulfone resin, and polyimide resin. Polysulfone resin is most preferable. There is provided O-rings 19 (one or two) between the inner surface of the main body 15 and a front surface of a stationary plate 20 of the transducer 3 so as to hold the transducer 3.

The lid 16 may be made of a material which is the same as that of the main body 15. Since the suction nipple 17 and the cable 5 pass through the lid 16 as described above, a gap can be easily formed in the lid 16. Therefore there is a fear of entering of water content such as cleaning liquid or the like into the main body 15. In order to prevent this, the gap must be sealed with an adhesive or the like. Therefore, it is preferable that the lid 16 is made of resin exhibiting an excellent adhesion capability such as polysulfone resin.

Since the irrigation nipple 14 and the suction nipple 17 are repeatedly connected to and disconnected from the irrigation tube 9 and the suction tube 11, respectively for every treatment, they are preferably made of a material exhibiting high strength and corrosion resistance. Stainless steel type metal or polysulfone resin are preferable.

As shown in FIG. 3 in detail, a front plate 21 and a backing plate 22, both of which are made of duralmin or titanium alloy, are respectively disposed on opposite ends of the transducer 3 made of PZT (plumbeous zirconate titanate). The transducer 3 is clamped by a bolt (not shown) between the front plate 21 and the backing plate 22 to form a so-called bolt langevin transducer (BLT) structure. A flange portion 20 is formed on the front plate 21. The transducer 3 is secured in the main body 15 through the flange portion 20 by means of a pin, an adhesive or a screw.

A nipple 23 is provided at an end portion of the backing plate 22. The nipple 23 is connected to the suction nipple 17 by a connection tube 24 made of a material exhibiting an excellent elasticity and heat resistance such as fluoro rubber and silicon rubber. It is preferable that the horn 2 is made of metal of noncorrosive and exhibiting an excellent tension resistance such as duralumin and titanium alloy. Preferably, the horn 2 has a length substantially equal to integral multiple of $\frac{1}{2}$ of the wavelength of ultrasonic to be generated. A suction passage 25 is provided to extend in an axial direction through the horn 2, the front plate 21, the transducer 3, the backing plate 22, the transducer nipple 23, and the suction nipple 17. The transducer 3 has a plurality of electrodes 26 to which high-frequency electric power generated by the oscillator 4 is supplied through the cable 5. As a result, the transducer 3 is vibrated in a ultrasonic manner in an axial direction, causing the ultrasonic vibration to be transmitted to the horn 2.

Referring back to FIG. 1, reference numeral 6 represents a roller type irrigation pump for pumping cleaning liquid into the insert 1 from a cleaning liquid container 7, which is of isotonic to the body fluid such as physiological saline solution, or innocuous clyster fluid. A pre-heater 8 heats the cleaning liquid in advance up to the degree which is substantially the same as that in the rectum, for example, 35° C. to 42° C. The preheater 8 may be disposed at any portion between the insert 1 and the cleaning liquid container 7. It is preferable that it is positioned between the cleaning liquid container 7 and the irrigation pump 6 since it is not subjected to any pumping pressure from the irrigation pump 6. In addition, the irrigation pump 6 can be omitted from the structure if the cleaning liquid container 7 is disposed at a position higher than that of the insert 1, for example by 50 cm to 100 cm since the cleaning liquid can be allowed to flow due to the potential energy. The irrigation tube 9 for supplying the cleaning liquid is made of soft vinyl chloride resin or silicon resin. However, it is not limited to these resins, and it may be made of various types of resin so far as it has a proper elasticity and it is not deteriorated or the components thereof cannot be solved by the cleaning liquid.

A reservoir container 10 is disposed between the insert 1 and the suction pump 12 for the purpose of extracting and reserving the excretions such as the excrements, through the suction tube 11, which have been crushed by the horn 2 disposed at the end portion of the insert 1. The reservoir container 10 is able to accommodate therein a plastic container, a glass bottle, or a disposable plastic bag. The reservoir container 10 can endure the negative suction pressure of 0 mmHg to -760 mmHg generated by the suction pump 12. The suction tube 11 is made of soft vinyl chloride resin or silicon resin, which can endure the negative pressure generated by the suction pump 12 and as well exhibit a proper flexibility.

Then, the operation of the excretions treating apparatus described above will be explained hereinunder.

First, the straight portion 27 of the protection cover 13 of the insert 1 is inserted into the rectum through the anus by a proper length. Then, the cleaning liquid such as physiological saline solution is injected into the rectum through the irrigation nipple 14. Simultaneously, high-frequency electric power is supplied from the oscillator 4 to the transducer 3 to ultrasonically vibrate the end portion of the horn 2 in the axial direction thereof and thereby to crush the excrements. The excrements can be emulsified by cleaning liquid with a cavitation phenomenon. The emulsified excrements are extracted through the suction passage 25, the suction nipple 17, and the suction tube 11 by the negative pressure generated by the suction pump 12, and are discharged into the reservoir container 10 as to be reserved therein. Since the excrements in the rectum are crushed and sucked to be removed, the rectum gradually contracted. As a result, the excrements are successively pushed to the end portion of the horn 2. Accordingly, a whole excrements in the rectum are crushed and sucked to be removed.

The frequency of the ultrasonic generated by the oscillator 4 is 17 KHz to 40 KHz, preferably 18 KHz to 23 KHz. According this, the length of the straight portion 27 of the protection cover 13 can be elongated, which is to be inserted into the rectum through the anus can, and as well the oscillating amplitude of the horn 2 can be enlarged. The power required for generating the ultrasonic is 100 W to 1 KW, preferably 200 W to 500 W. The oscillating amplitude of the horn 2 is 40 μm to 300 μm, preferably 100 μm to 200 μm.

Figure 4A:
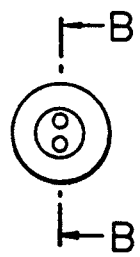
FIGS. 4A, 5A, 6A, 7A and 8A are side-elevational views showing end portions of the horns according to other embodiments, respectively.
Figure 4B:
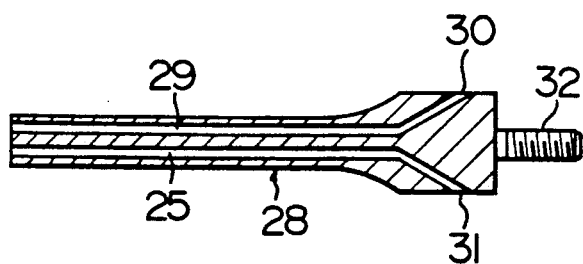
FIGS. 4B, 5B, 6B, 7B, and 8B are cross-sectional views taken along the line B—B of corresponding FIGS. 4A, 5A, 6A, 7A and 8A, respectively.

FIG. 4 shows an embodiment in, which a cleaning liquid passage 29 and a suction passage 25 are formed in a horn 28. The cleaning liquid is introduced into a cleaning liquid passage 29 through an irrigation nipple joint port 30 formed at a rear end portion of the cleaning liquid passage 29, and is directly injected to the excrements from the end portion of the horn 28. The excrements crushed by the ultrasonic oscillation of the horn 28 pass through the suction passage 25, and are sucked to be discharged outside the rectum through a suction nipple joint port 31. The suction passage 25 may be formed to pass through a threaded portion 32.

According to this embodiment, since the cleaning liquid can be directly injected to the excrements from the end portion of the horn 28 which has been inserted into the excrements, the emulsifying speed of the excrements can be significantly raised.

The embodiments shown in FIGS. 5B to 8B have an intention that the working efficiency is improved by increasing a contact area between the end portion of a horn 51 and the excrements and that the clogging of the suction passage with the crushed excrements is prevented.

Figure 5A:
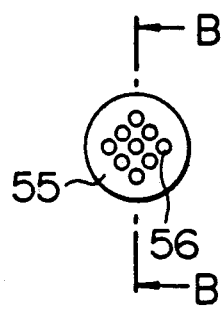
Figure 5B:
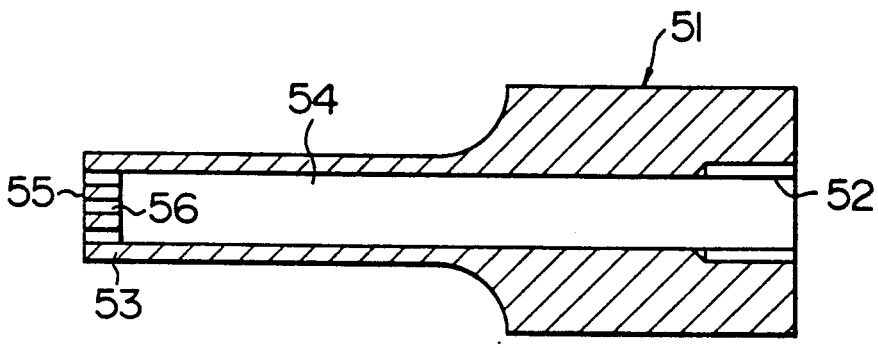

According to the embodiment shown in FIG. 5B, a suction passage 54 extends through a horn 51 at an end portion of which is provided with an insulating wall 55 having one or a plurality of apertures 56. As a result, the contact area between the excrements and the end portion of the horn 51 can be increased so that the crushing efficiency can be significantly improved. Furthermore, a problem of clogging in the horn 51 with the crushed excrements can be overcome since the diameter of the aperture 56 at the front end portion is smaller than that of the suction passage. The thickness of the insulating wall 55 is 0.5 mm to 25 mm, preferably 1 mm to 10 mm.

Figure 6A:
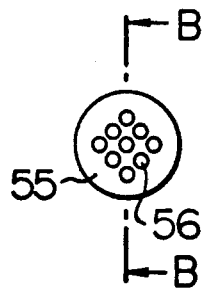
Figure 6B:
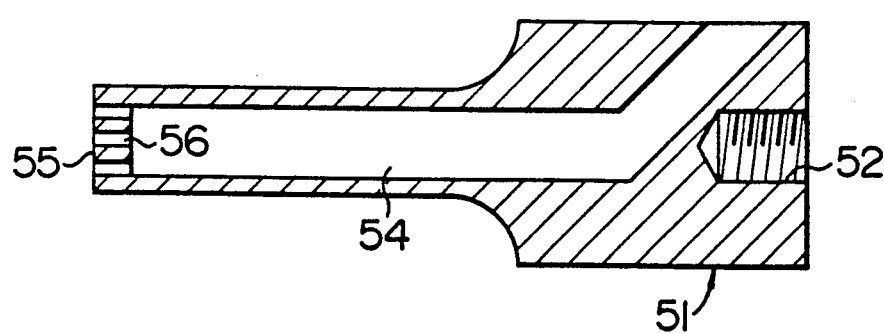

FIG. 6 shows an embodiment in which a suction passage 54 is opened in an outer peripheral surface of a rear end portion of a horn 51. According to this embodiment, the suction passage 54 opened in the outer peripheral surface is connected to a metal tube or a plastic tube arranged along the side portion of an ultrasonic operating instrument via a nipple (not shown). The crushed and emulsified tissue is directed outside the horn and discharged therefrom.

Figure 7A:
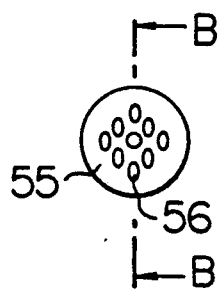
Figure 7B:
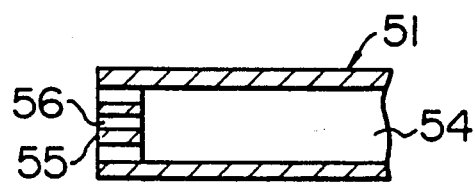
Figure 8A:
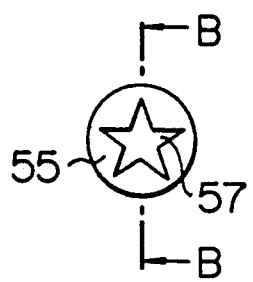
Figure 8B:
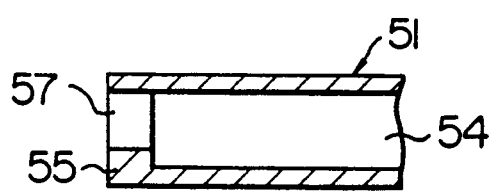

The cross-sectional shape of the aperture 56 formed in the insulating wall 55 is not limited to particularly a circular one. It may be an oval shape as shown in FIG. 7A. Instead of one or a plurality of the apertures, a star-like shape aperture 57 or polygonal aperture may be provided.

Figure 9:
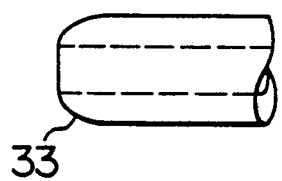
FIGS. 9, 10, and 11 are side elevational views showing end portions of the horns, according still another embodiments, respectively.
Figure 10:
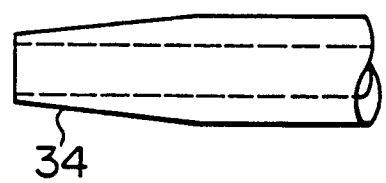
Figure 11:
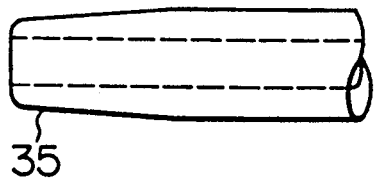

Embodiments shown in FIGS. 9 to 11 have a purpose of protecting the anal wall from a damage when the horn is inserted into the rectum through the anus. The shape of the end portion of a horn 33 shown in FIG. 9 presents a spheric one or an oval spheric one. The end portion of a horn 34 shown in FIG. 10 is tapered. FIG. 11 shows an embodiment in which the end portion of a horn 35 presents a shape obtained by combining a spherical shape and a tapered shape. Any of the above-described shapes makes it easy to insert the horn into the anus and to prevent the horn from damaging the anal wall.

As a material of the horns described above, non-corrosive metal is preferable, such as titanium alloy, aluminum alloy or stainless steel. Furthermore, such material preferably must have a sufficient strength for ultrasonic vibration. Carbon fiber reinforced metal obtained by mixing metal such as aluminum and carbon fibers, carbon fiber reinforced plastic obtained by mixing polysulfone plastic and carbon fibers, and garphite can be used as the material.

Figure 12A:
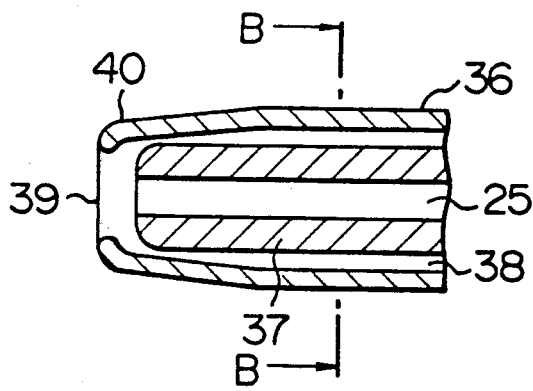
FIG. 12A is a fragmentary cross-sectional view of an end portion of an insert according to other embodiment.
Figure 12B:
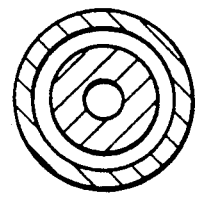
FIG. 12B is a cross-sectional view taken along the line B—B of FIG. 12A.

According to other embodiment shown in FIGS. 12A and 12B, a protection cover 36 extends beyond an end portion of a horn 37. According this, the end portion of the horn 37 which is mechanically vibrated in ultrasonic manner is prevented to contact with mucous membrane of the rectum wall. The cleaning liquid is injected into the excrements from an opening 39 formed at an end of the protection cover 36 through a tubular cleaning liquid passage 38 defined between the horn 37 and the protection cover 36. The excrements which has been crushed and emulsified by the ultrasonic vibration at the end portion of the horn 37 passes through the suction passage 25 to be discharged outside the patient's body. An end portion 40 of the protection cover presents a spherical shape, and a tapered shape for the purpose of facilitating insertion into the anus. The distance between an end of the opening 39 at the end portion of the protection cover 36 and an end of the horn 37 is 0.5 mm to 10 mm, preferably 1 mm to 5 mm in order to prevent the cleaning liquid from being directly sucked into the suction passage 25.

Figure 13A:
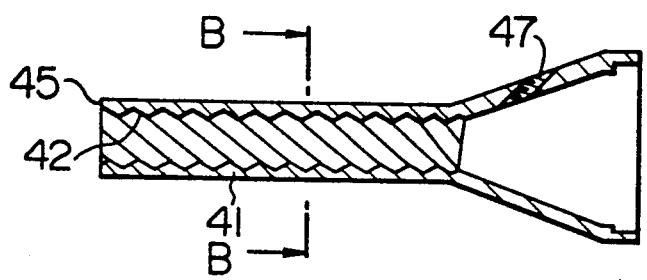
FIGS. 13A and 14A are cross-sectional views showing protection covers according to other embodiments, respectively.
Figure 13B:
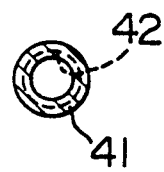
FIGS. 13B and 14B are cross-sectional views taken along the line B—B of FIGS. 13A and 14A, respectively.

A protection cover 41 of other embodiment shown in FIG. 13A is provided on an inner surface thereof with spiral grooves 42. The number of the spiral grooves is not limited particularly, but preferably 2 to 3 in terms of manufacturing easiness and smooth injection of the cleaning liquid from an end portion 45 of a protection cover 41.

Figure 14A:
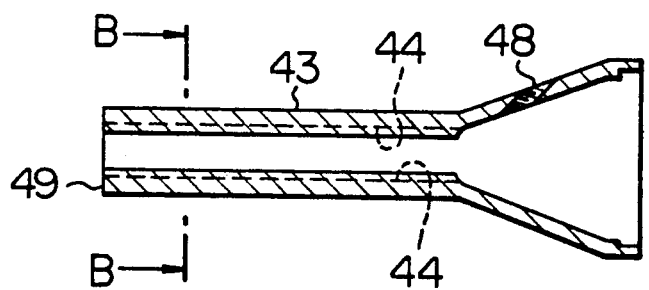
Figure 14B:
Figure 15A:
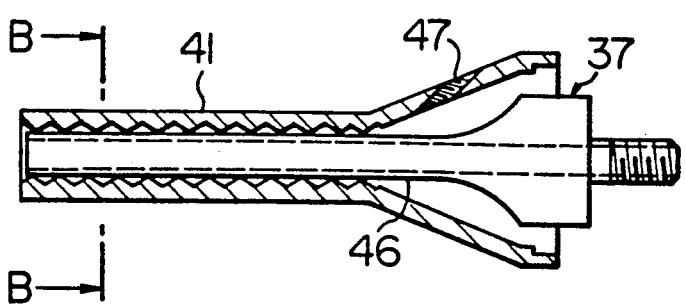
FIG. 15A is a cross-sectional view showing an end portion of an insert according to other embodiment.
Figure 15B:
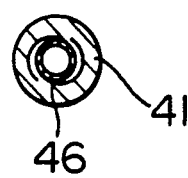
FIG. 15B is a cross-sectional view taken along the line B—B of FIG. 15A.

According to an embodiment shown in FIG. 14A, there is provided a plurality of axial slits 44 on an inner surface of a protection cover 43. The cross sectional shape and the number of the slits 44 are not limited particularly, but the cross section of the front portion of the protection cover 43 may preferably be a star-like shape as shown in FIG. 14B.

These spiral grooves 42 and the slits 44 are preferably so sized that inner surfaces thereof bring into contact with an outer surface of a staright portion 6 of the horn 37. According to these embodiments, the cleaning liquid injected from the irrigation nipple which is screw mounted to irrigation nipple thread 47 or 47 passes through a space defined between the horn 37 and the spiral groove 42 or the slit 44, and then is injected from the end portion 45 or 49 of the protection cover towards the excrements. Therefore, heat generated in the horn 46 due to the mechanical ultrasonic vibration thereof can be efficiently cooled down, and as well the protection cover 41 or 43 can hardly misalign with regard to an axis of the horn 37 when inserted into the anus.

INDUSTRIAL APPLICABILITY

According to the present invention, since the excrements in the rectum can be crushed, and sucked to be removed, evacuation can be efficiently completed with respect to the conventional excretion means.

In addition, even if the excrements is hard, which is very difficult to be evacuated, a complete evacuation can be readily conducted in a short time period by the excretions treating apparatus according to the present invention. It is within the scope of the present invention to reverse the uses of the above mentioned suction passage and the annular passage for cleaning liquid.

According to another aspect of the present invention, since the contact area between the horn and the excrements is increased by providing an insulting wall at the end portion of the horn, the excrements crushing efficiency can be improved, and thereby the evacuation efficiency also be improved In addition, it is hardly to clog the suction passage formed in the horn with crushed excrements. The rectum wall can be protected from damage.

Since the excretions treating apparatus according to the present invention is formed in a closed system insulated from the circumstances, any adverse effect on the circumstances such as bad odor or smell can be prevented.

We claim:

1. An excretions treating apparatus for evacuating excrements in a rectum comprising an insert accomodating a horn which is mechanically vibrated by ultrasonic oscillation means, irrigation means for injecting cleaning liquid into the rectum, and means for excreting and removing excrements which has been crushed and emulsified, wherein said irrigation means includes a preheater for previously heating said cleaning liquid.

2. An excretions treating apparatus for excrements in a rectum said apparatus comprising:
    an insert including a horn capable of being mechanically vibrated by ultrasonic oscillation means and a protective cover disposed around said horn to define therebetween a tubular space;
    a suction passage provided within said horn, which opens at one end of said horn;
    an insulating wall disposed in an opening portion in said suction passage and provided with one or more through apertures;
    irrigation means for injecting cleaning liquid into the rectum, said irrigation means communicated with said tubular space through which the cleaning liquid flows;
    means for excreting and removing excrements which has been crushed and emulsified, said excreting and removing means communicated with said suction passage.

3. An excretions treating apparatus according to claim 2, wherein said insulating wall includes a plurality of through apertures, cross sections of which are circular, elliptic, or polygonal.

4. An excretions treating apparatus according to claim 2, wherein said insulating wall includes a one through aperture, a cross section of which is starlike.

5. An excretions treating apparatus according to claim 2, wherein said one end of said horn presents a spheric shape.

6. An excretions treating apparatus according to claim 2, wherein said horn is made of titanium alloy or aluminum alloy.

7. An excretions treating apparatus according to claim 2, wherein said protection cover extends beyond said horn.

8. An excretions treating apparatus according to claim 2, wherein an end portion of said protection cover presents a spheric shape.

9. An excretions treating apparatus according to claim 7, wherein an end portion of said protection cover presents a spheric shape.

10. An excretions treating apparatus to claim 2, wherein a plurality of spiral grooves or a plurality of axial grooves are provided on an inner peripheral surface of said protection cover.

11. An excretions treating apparatus according to claim 7, wherein a plurality of spiral grooves or a plurality of axial grooves are provided on an inner peripheral surface of said protection cover.

12. An excretions treating apparatus according to claim 8, wherein a plurality of spiral grooves or a plurality of axial grooves are provided on an inner peripheral surface of said protection cover.

13. An excretions treating apparatus according to claim 9, wherein a plurality of spiral grooves or a plurality of axial grooves are provided on an inner peripheral surface of said protection cover.

14. An excretions treating apparatus according to claim 2, wherein said protection cover is made of plastic, synthetic rubber, natural rubber or a combination thereof.

15. An excretions treating apparatus according to claim 7, wherein said protection cover is made of plastic, synthetic rubber, natural rubber or a combination thereof.

16. An excretions treating apparatus according to claim 8, wherein said protection cover is made of plastic, synthetic rubber, natural rubber or a combination thereof.

17. An excretions treating apparatus according to claim 2, wherein said irrigation means includes a preheater for previously heating said cleaning liquid.

18. An excretions treating apparatus according to claim 2, wherein said excreting and removing means includes a reservoir container for excrements, in which a plastic bag is accommodated.

* * * * *